United States Patent [19]

Hoekema et al.

[11] Patent Number: 5,149,645

[45] Date of Patent: Sep. 22, 1992

[54] PROCESS FOR INTRODUCING FOREIGN DNA INTO THE GENOME OF PLANTS

[75] Inventors: André Hoekema, Brisane; Paul J. J. Hooykaas, Leiden; Robert A. Schilperoort, Anthonie Duycklaan 10c 2334 CD, Leiden, all of Netherlands

[73] Assignees: Rijksuniversiteit Leiden; Robbert Adriaan Scilperoort, both of Leiden, Netherlands

[21] Appl. No.: 449,282

[22] Filed: Dec. 5, 1989

Related U.S. Application Data

[63] Continuation of Ser. No. 737,154, May 23, 1985, abandoned.

[30] Foreign Application Priority Data

Jun. 4, 1984 [NL] Netherlands ............... 8491780

[51] Int. Cl.$^5$ ............ C12N 15/84; C12N 1/21; C12N 15/90
[52] U.S. Cl. .................. 435/172.3; 435/252.2; 435/252.3; 435/320.1; 435/319.1; 935/30; 935/55; 935/67; 935/72; 935/22; 935/24
[58] Field of Search ............... 435/172.3, 317.1, 252.3, 435/320.1; 935/22, 24, 30, 55, 67, 72; 800/205

[56] References Cited

PUBLICATIONS

McClure 1985 Ann. Rev. Biochem. 54:171–204.
Wang 1985 Ann. Rev. Biochem. 54:665–697.
Cocking et al. (1987) Science 235:1259–62.
Christon et al (1986) Plant Physiol. 82:218–221.
de Framond et al. (1983) "Mini Ti: A New Vector Strategy for Plant Genetic Engineering" Biotechnology/-May 1983 pp. 262–269.
Barker et al 1983 Pl Molec Biol 2:335–350.
Hoekema et al 1983 (May) Nature 303:179–180.
Herrera-Estrella et al 1983 (Jun.) EMBO J 2:987–995.
Strickberger 1976 in Genetics, MacMillan Publishing Co., Inc. pp. 398–402.
De Cleene et al, The Botanical Review, vol. 42, pp. 389–412 and 463–466 (1976).
Hooykaas et al, Nature, vol. 311, pp. 763–764 Oct. 25, 1984.
Christou et al, Plant Physiol., vol. 82, pp. 218–221, (1986).
Hooykaas, P. J. J. et al, Transfer of the Agrobacterium tumefacines . . . ex planta (1977) 98,447–484.
Hoekema, A. et al, Delivery of T-DNA . . . plant cells (1984), vol. 3 No. 11, 2485–2490.
Agrobacterium Tumefaciens-Mediated . . . Radiata, Y. Jianping et al, GMICN 4(1):86–91, 1988.
In vitro transformation . . . by Agrobacterium tumefaciens, Marton et al, reprinted from Nature, vol. 277, No. 5692, pp. 129–131, Jan. 11, 1979.
Plant Cell Protoplasts-Isolation and Development, Edward C. Cocking, Ann. Pev. Plant Physiol 1972, 23:29–50 pp. 29–50.
An Introduction to Plant Biology T. E. Weiler et al, Botany, Fifth Ed., 1974, pp. v, 32–33.
Molecular Biology of the Cell B. Alberts et al, 1983 Ed., p. 1142.

(List continued on next page.)

Primary Examiner—Elizabeth C. Weimar
Assistant Examiner—P. R. Rhodes
Attorney, Agent, or Firm—Ladas & Parry

[57] ABSTRACT

Process for introducing foreign DNA into the genome of plants by infecting plants or explantates thereof or plant protoplasts or by incubating plant protoplasts with *Agrobacterium*, in which Agrobacteria are used, which contain one or more T-regions and a Vir-region from the Ti-plasmid of Agrobacterium in their genetic material and/or one or more T-regions comprising an artificial T-region which consists of each DNA desired, flanked by border sequences as present in the wild type T-region of Agrobacterium or sequences being functionally analogous thereto.

6 Claims, 3 Drawing Sheets

OTHER PUBLICATIONS

Gene Tagging in Plants by a T-DNA insertion mutagen that generates APH (3') II–Plant Gene Fusions by Andre et al. Mol. Gen Genet (1986) 204:512–518.

Isolation of Tobacco DNA Segments with Plant Promoter Activity by Herman et al, Molecular and Cellular Biology, Dec. 1986, pp. 4486–4492.

The Uses of Isolated Protoplasts in Plant Genetics by D. J. Cove, Heredity (1979) 43(3)295–314.

The Host Range of Crown Gall, M. DeCleene and S. DeLey, The Botanical Review, Oct.–Dec. 1976, vol. 42, No. 4 pp. 389–401 and 462–465.

An Agrobacterium-transformed cell culture from the monocot Asparagus officinalis, J. Hernalsteens et al, The EMBO Journal, vol. 3, No. 13, pp. 3039–3041, 1984.

Expression of Ti-plasmid Genes in Monocotyeledonous Plants Infected with Agrobacterium Tumefaciens by Hooykaas-Van Slogteren et al, reprinted from Nature, vol. 311, No. 5988 pp. 763–764, Oct. 25, 1984.

Identification of Plant Promotacs in Situ by T-DNA Mediated Transcriptional Fusions to the npt-II Gene by Teer et al, The EMBO Journal vol. 5, No. 8, pp. 1775–1760, 1986.

Montagu et al, Current Topics in Microbiology & Immunology, vol. 96, pp. 237–254 (1982).

De Greve et al, Nature, vol. 300, pp. 752–754, Dec. 1982.

Christou et al, Biosis Abstrac 83:18043, (1986).

DeCleene et al, 1981, Botanical Review 47(2):pp. 147–194.

Hoekema et al, 1983, Nature 303:179–180.

Gross et al, Journal of Gen. Microbiology, (1979) 115, pp. 479–489.

Leemans et al, Molecular Biology of Plant tumors, pp. 537–543.

Hille, J. Bacteriology, 154:693.

Flavell et al, Nature 307:108 (1984).

Graves et al, Plant Biology, vol. 7, pp. 43–50, 1986.

Grimsley et al, Nature, vol. 325, pp. 177–179, Jan. 8, 1987.

Hernalsteens et al, The EMBO Journal, vol. 3, pp. 3039–3041, Dec. 20, 1984.

Herrera-Estrella et al, The EMBO Journal vol. 2, pp. 987–995, (1983).

Herrera-Estrella et al, Nature, vol. 303 pp. 209–213 (May 1983).

Zambryski et al, The EMBO Journal, vol. 2, pp. 2143–2150 (1983).

Van Haute et al, The EMBO Journal, vol. 2, pp. 411–417 (1983).

Leemans et al, Molecular and Applied Genetics, vol. 1, pp. 149–164 (1981).

Caplan et al, Science, vol. 222, pp. 815–821, Nov. (1983).

Nester & Kosuge, Ann. Rev. Microbiol. 1981 34:531–65.

DeCleene and De Ley, The Botanical Review, vol. 47, Apr.–Jun. 1981, pp. 147–186.

Lippincott et al, Ch. 68 from the Prokaryotes; Handbook on Habitats (1981) pp. 842–852.

De Smedt & De Ley, Int. Journal of Sys. Bacteriology, Jul. 1977, pp. 222–240.

Grimsley et al, Biotechnology, vol. 6, Feb. 1988, pp. 185–187.

Bytebier et al, Proc. Nat'l. Acad. Sci., U.S.A., Genetics, vol. 84, pp. 5345–5349, Aug. 1987.

Depicker et al, Mol. Gen. Genet (1985) 201:477–484.

Den Elzen et al, Plant Molecular Biology, 5:149–154 (1985).

An, G.; Plant Physiol. (1985) 79,568–570.

Paszkowski et al, The EMBO Journal, vol. 3, No. 12, pp. 2717–2722 (1984).

Czernilofsky et al, DNA, vol. 5, No. 2, 1986 pp. 101–113.

Hain et al, MGG (1985) 199:161–168.

Perrbolte et al, Plant Molecular biol. 5:235–246, 1985.

Deshayes et al, The EMBO Journal, vol. 4, No. 11, pp. 2731–2737, 1985.

de la Pena et al, Nature, Jan. 15, 1987, pp. 274–277, vol. 325.

Schafer et al, Nature, vol. 327, Jun. 11, 1987, pp. 529–532.

Agrios, Plant Pathology, 3rd Ed., Academic Press, Inc., 1988, p. 559.

Kalil et al, Neoplasms-Comparative Pathology of Growth in Animals, Plants & Mans, vol. 49, pp. 813–821.

De Cleene, Phytopath Z., 113, 81–89 (1985).

Schell et al, Bio/Technology, Apr. 1983, Review Article, pp. 175–180.

Prinsen et al, Plant Cell Physiol. 31(1):69–75 (1990).

Drummond, Nature, vol. 303, May 19, 1983, pp. 637–642.

Klee et al, Bio/Technology, vol. 3, Jul. 3, 1985, pp. 637–642.

Deng et al, Science in China, vol. 33, No. 1, Jan. 1990, pp. 27–34.

Deng et al, Chinese Science Bulletin, vol. 34, No. 21, Nov. 1989, pp. 1817–1819.

Raineri et al, Bio/Technology, vol. 8, Jan. 1990, pp. 33–38.

Jianping et al, GM ICN 4(1):86–91, 1988, pp. 86–91.

Dale et al, Plant Science, 63 (1989) pp. 237–245.

Marks et al, Plant Science, 63(1989) pp. 247–256.

Hayes et al, J. General Virol. (1988), 69, 891, 896.

FIG. 4

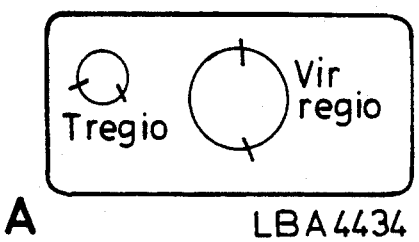

A    LBA4434 normal tumours on dicotyledonous plants (Dutch patent appl. 83.00698) and also transformation of monocotyledonous plants (Dutch patent appl. 84.01048)

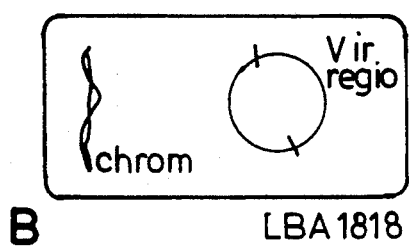

B    LBA1818 no transformation of higher plant cell

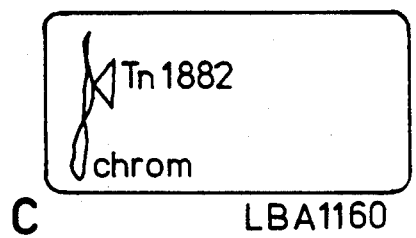

C    LBA1160 no transformation of higher plant cell

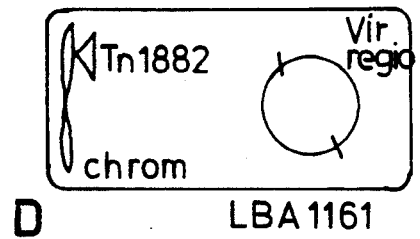

D    LBA1161 transformation of higher plant cell does occur

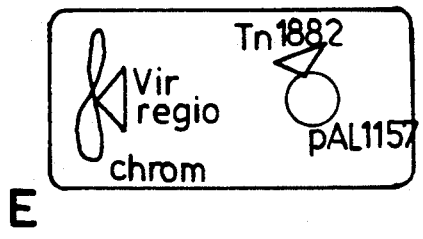

E transformation of higher plant cell does occur

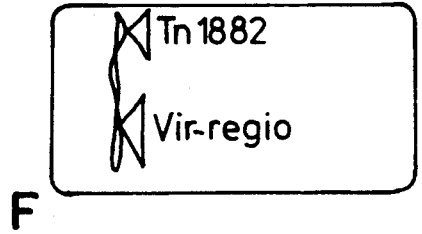

F transformation of higher plant cell does occur

PROCESS FOR INTRODUCING FOREIGN DNA INTO THE GENOME OF PLANTS

This is a continuation of application Ser. No. 06/737,154, filed May 23, 1985, now abandoned, which is incorporated herein by reference.

FIELD OF THE INVENTION

The invention relates to improvements in Agrobacterium strains suitable for genetic manipulation of higher plant cells.

BACKGROUND OF THE INVENTION

A large plasmid (Ti-plasmid), present in nature in tumour provoking strains of *Agrobacterium tumefaciens*, is responsible for tumour induction in dicotyledonous plants (Van Larebeke et al., Nature (London) 252, 169-170 (1974)l Zaenen et al., F. Mol. Biol 86, 109-127 (1974)). A specific part of the Ti-plasmid, called T-region, is transferred by the bacterium to the plant cell and is integrated into the core DNA (Chilton et al., Cell 11, 263-271 (1977)).

The integrated DNA is expressed (Willmitzer et al., Mol. Gen. Genet. 182, 255-262 (1981)) and this expression forms the molecular basis of the plant disease Crown Gall. Resulting tumour cells, in contradistinction to normal plant cells, can be grown on synthetic media without adding the plant hormones auxine and cytokinine. (UBraum, Proc. Natl. Acad. Sci 44, 344:349 (1958)). The tumour cells also contain specific compounds, called opines, which are not present in normal cells, the genetic information of which lies coded on the transferred T-DNA (Bomhoff et al., Mol. Gen. Genet. 145, 177:181 (1976); Schroder et al., FEBS Lett. 129, 166-168 (1981)).

Besides the T-region, which is found in the plant cell, the Ti-plasmid contains a second region which is essential for the virulence qualities of the bacterium (Omms et al., J. Bacteriol. 144, 82-91 (1980; Garfinkel et al., J. Bacteriol. 144, 732-743 (1980)). This region was never seen in tumour cells and genetic analyses have shown that mutations in this area (leading to much weakened virulence or complete avirulence) are trans complementable by wild types of genes, which are present on clones or R Prime Plasmids (Hille et al. Plasmid 7, 197-118 (1982); Klee et al., J. Bacteriol. 150, 327-331)). Seven genetic loci have been determined in this Vir (Virulence) region, called Vir A, B, C, D, E, F and G (Klee et al., J. Bacteriol. 150, 327-331 (1982); Hille et al., Plasmid 7, 107-118 (1982); Hooykaas et al., in press (1984)).

The Vir region and the T-region can be physically separated from one another on two compatible plasmids without any negative effect on the capacity of agrobacteria to incorporate the T-region or artificial T-region into the plant cell (Hoekema et al., Nature (London), 303, 179-180 (1983)). A binary vector system based on this invention can be used for the genetic manipulation of plant cells. (Described in Dutch patent specification no. 83 00698 and European patent application no. 842002396, and in Dutch patent application 84 01048). In Dutch patent application 84 01048 we reported that monocotyledonous species, which was thought not to be susceptible to Agrobacterium, was indeed able to respond to Agrobacterium. After wounding the plants and infecting with Agrobacterium it appeared from the experiments that (1) cells of monocotyledonous plants were positively transformed by *A. tumefaciens;* (2) plant material isolated from non-wounded or wounded but not infected monocotyledonous plants contained neither octopine nor nopaline. Opines were not discovered in plant material isolated from plants infected with avirulent strains while plant cells obtained from wound sites infected with virulent *A. tumefaciens* strains appeared to nearly always contain opines. Consequently, it was concluded that the Ti plasmid is suitable as a vector for monocotyledonous plant cells.

SUMMARY OF THE INVENTION

The T-region of the Ti (tumour inducing)- and Ri (root inducing) - plasmid of Agrobacterium is transferred in nature to cells of higher plants, where this DNA is introduced into the genome and is expressed. Transfer of the T-region or any artificial T-region also occurs when this region is present in the bacterium on a separate plasmid, next to a plasmid which contains the essential virulence genes on a Vir-region. (This is the so-called binary vector system described in Dutch patent application no. 83 00698, and also mentioned in Dutch patent application no. 8401048 for genetic manipulation of monocots.) The surprising, novel invention now described is based on an extension of the binary vector system. In the invention, an intact T-region or artificial T-region is introduced into the chromosome of Agrobacterium as part of a transposon (Tn 1882) with a Vir-region present on an auxiliary plasmid. The T-region introduced into the bacterial chromosome in this way appears to be transferred to plant cells efficiently, where it is integrated into plant genomes and is expressed. This invention demonstrates that the binary system aforementioned could also be used by introducing the Vir-region into the bacterial chromosome with the T-region present on a plasmid or by introducing the Vir-region and the T-region into the bacterial chromosome of Agrobacterium. With this new invention new procedures can be developed for genetic manipulation of dicotyledonous and monocotyledonous plant cells. The invention creates new possibilities for the incorporation of foreign DNA into the genome of dicotyledonous and monocotyledonous plant cells; a binary vector system that can be used in Agrobacterium, wherein one of the components or both components are no longer present as loose replicons in the bacterium.

The result presented here shows that the presence of the components of the binary system on plasmids is not an essential condition. The components (T- or Vir-region) can be integrated separately or together into the chromosome of Agrobacterium without any negative effect on the transfer of the T-region or artificial T-region to plant cells followed by integration into plant genomes. The invention not only throws a vivid light on the molecular mechanism which enables the bacterium to transfer DNA to plant cells, it also broadens the possibilities for genetic manipulation of higher plants which are offered by the binary system.

DETAILED DESCRIPTION

Figure 1:
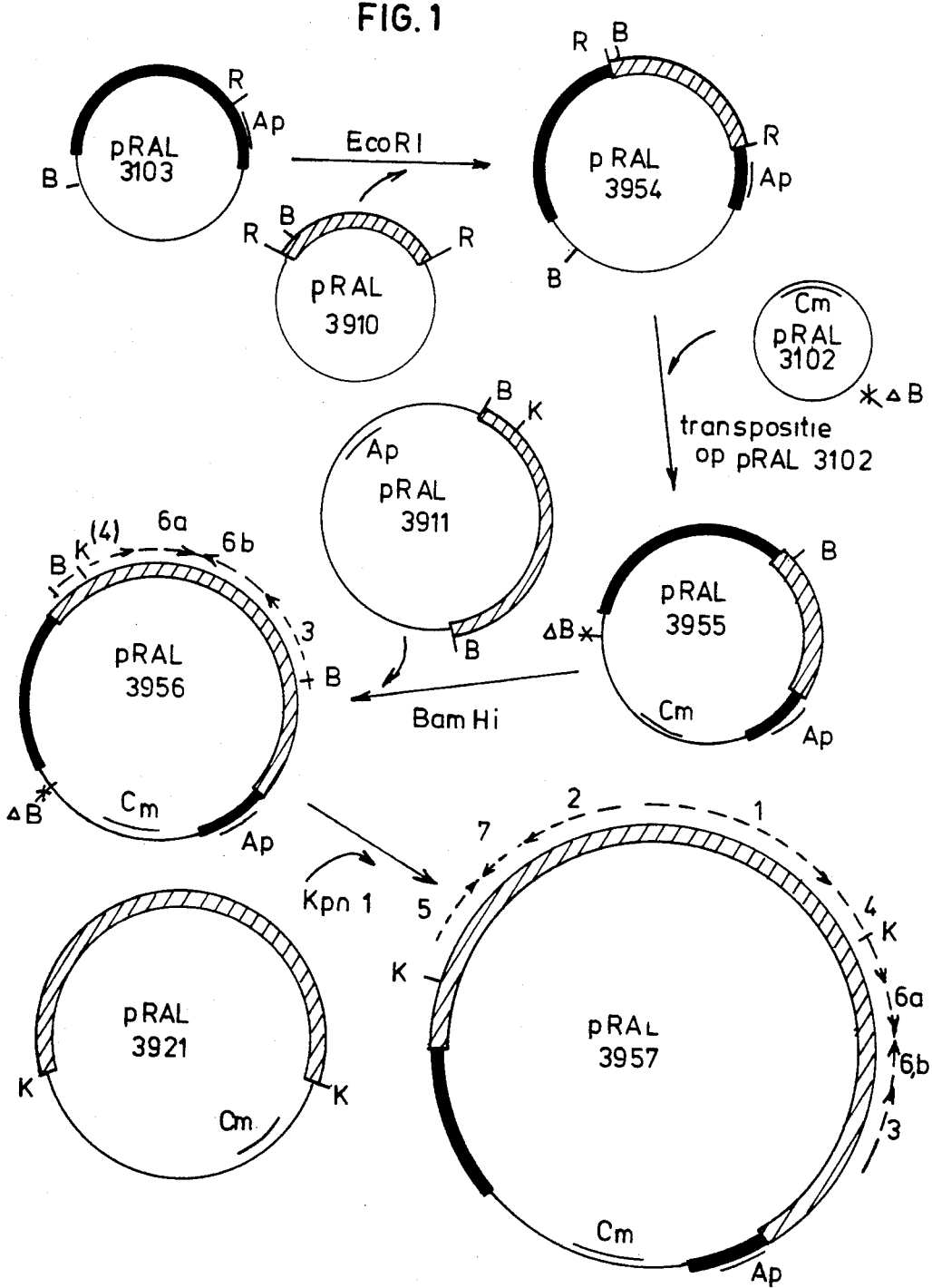

In order to insert, the T-region of the Ti plasmid at different locations into the genome of Agrobacterium, the transposon Tn 1882 (containing the entire T-region) was constructed in vitro. Three restriction enzyme-fragments which together comprise the entire T-region, EcoRI fragment 10a, BamHI fragment 17a and KpnI fragment 9, were separately subcloned and used in a three-stage-cloning to construct the intact T-region, as described hereunder, in transposon Tn3 (5-65). This transposon (Kostriken et al., Proc. Natl. Acad. Sci 78, 4041-4045) is a derivative of Tn3 into which an EcoRI-site is introduced at a location which is not essential for transposition of the transposon or its ampicilline resistence. This transposon was further inserted into the *E coli* vector plasmid pTR262 (Roberts et al., Gene 12, 123-127 (1980)) that does not contain an EcoRI site. In the unique EcoRI site of the resulting plasmid pRAL 3103 the EcoRI fragment 10a of pTiB6 was cloned. In the next stage BamHi fragment 17a, which partly overlaps with EcoRI fragment 10a, was positioned in the natural BamHI site (position 13.774 according to Barker et al., Plant. Mol. Biol. 2, 335-350 (1983)). For this purpose the Tn3 derived transposon with EcoRI fragment 19a was first transmitted to pRAL 3102, a plasmid from which the BamHI site was removed by means of in vitro deletion. To reach this plasmid pRAL 3102 was transformed to an *E.coli* strain where PAL 1155 (R 772::Tn 1880) was present. The resulting strain was used as a donor in a cross-fertilization to an *E.coli* strain without a plasmid. Selection for mobilization of pRAL 3102 by pAL 1155 provided 2 types of transconjugants. The transconjugants in which Tn 1880 were introduced into pRAL 3102 were purified by isolating plasmid DNA and using this DNA again for transformation of an *E.coli* strain without a plasmid for the markers of pRAL 3102 and Tn 1880. Thus pRAL 3955 was obtained on which the transposon Tn 1880 is positioned. In the unique BamHi site of Tn 1880 on the plasmid 3955 BamHI fragment 17a was cloned in the correct orientation (see FIG. 1). Plasmid pRAL 3956 resulting therefrom contains the T-region genes 3, 6a, 6b and the right hand part of gene 4 as an uninterrupted piece of DNA present on a transposable element. Next, the KpnI fragment 9 was cloned in the correct orientation and in the natural position (position 9834) in the unique KonI site of pRAL 3956. The plasmid pRAL 3957 thus obtained contains the transposon Tn 1882 which comprises the intact T-region of the TiB6 plasmid.

In order to check whether Tn 1882 indeed contained a functional T-region Agrobacterium strains were constructed which contained the virulence plasmid pAL 4404 and a plasmid compatible therewith on which Tn 1882 was positioned. Therefore, Tn 1882 was inserted into plasmid R772. Plasmid R772 was cross-fertilized into an *E.coli* strain which contained pRAL 3957. Further cross-fertilizating to a strain without a plasmid with selection for transmission of the Ap$^R$ of Tn 1882, results in 2 kinds of transconjugants. This can be explained from the indication that plasmid R772 with low frequence pRAL 3957 could have mobilized, the other markers of pRAL being present in the transconjugants as well, or Tn 1882 could have landed on R772 by transposition. The presence of the transposon R772 in one of the 2 kinds of transconjugants was established by gel electrophoresis of plasmid DNA treated with restriction enzymes. The R772 plasmid with Tn 1882 thereon was called pAL 1157. Next the plasmid pAL 1157 was brought into LBA 4404 (pAL 4404) through conjugation. The tumourigenous qualities of LBA 4404 (Pal 4404, pLA 1157) appeared to be the same as those of the wild type *A.tumefaciens* strain LBA 1010 for all tested host plants. This result showed that transposon Tn 1882 comprised a normally functioning T-region.

For the insertion of Tn 1882 into the chromosome of *A.tumefaciens* different methods have been used. A first method comprised the construction in *E.coli* of the plasmid pRAL 3958. This plasmid has been derived from pRK 2013, a conjugative plasmid which cannot replicate in *A.tumefaciens*. This means that in principle pRAL 3958 (pRK 2013::Tn 1882) can be used as a "suicide plasmid" in *A.tumefaciens*, and then Tn 1882 can remain behind by transposition to the genome of the Agrobacterium strain, while pRAL 3958 itself gets lost. To reach this an *E.coli* strain with pRAL 3958 was used as a donor in a cross fertilization with *A.tumefaciens* strain LBA 288, which does not contain Ti plasmid.

Figure 2:
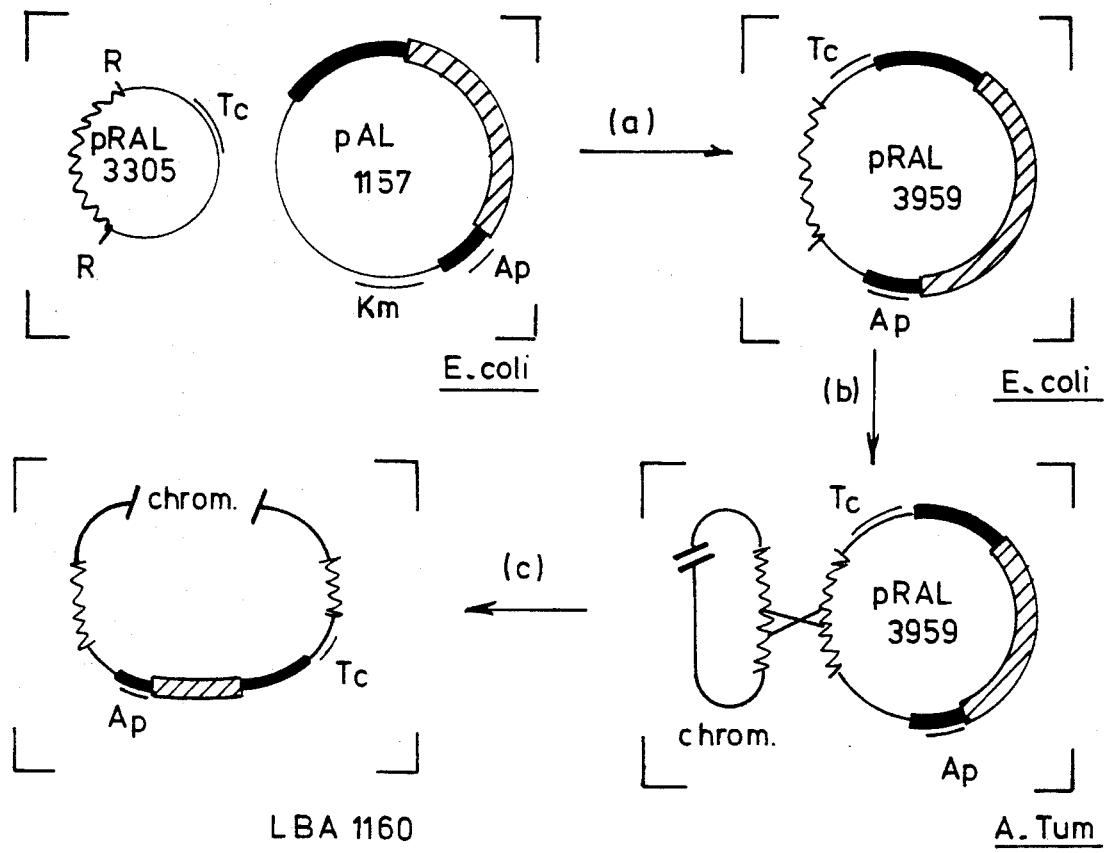

Although the resistence marker of Tn 1882 (Ap$^R$) is expressed very well in LBA 288 no transmission of the Ap$^R$ marker was found. Conjugative transmission of pRAL 3958 within *E.coli* occurred with a frequency of 30% per recipient. The negative result found for Agrobacterium indicates that Tn 1882 does not, or hardly ever, "leaps" into the genome of *A.tumefaciens*. We avoided this problem by applying a genomic piece of DNA of *A.tumefaciens* to a "suicide" donor plasmid for Tn 1882 first. The strategy comprised 3 stages (see FIG. 2): i) *A.tumefaciens* genomic DNA, isolated from LBA 288, was cloned in the *E.coli* vector pACYC 184 ii) in one of the clones, pRAL 3305, Tn 1882 was introduced by means of transposition in *E.coli* iii) the plasmid pRAL 3959 created this way cannot replicate in *A.tumefaciens* and can therefore be used for Tn 1882 in Agrobacterium as a "suicide" donor. Therefore pRAL 3959 was mobilized to LBA 288.

Now the Ap$^R$ of the Tn 1882 cannot only remain behind in Agrobacterium by possible transposition, but the entire plasmid can also enter the genome by homologous recombination with the cloned *A.tumefaciens* genomic DNA fragment. The mobilization to LBA occurred with a frequency of $10^{-7}$ per recipient, while (as a check) mobilization of this plasmid occurred within *E.coli* with a frequency of $10^{-4}$ per recipient. It appears from these results that pRAL 3959 can indeed not replicate in *A.tumefaciens*. One of the Agrobacterium transconjugants, LBA 1160, was analyzed in detail in order to establish whether Tn 1882 has indeed been introduced into the chromosome of Agrobacterium.

The piece of genomic DNA (pRAL 3305) cloned from Agrobacterium strain LBA 288 might have originated from the chromosome or from the cryptic plasmid pAt C58 which is present in LBA 288. Therefore, it is also possible that a possible recombination of pRAL 3959 in LBA 1160 could have occurred with the chromosome and the pAtC58. Strain LBA 1160 was genetically characterized (i and ii) and the DNA of the strain was analyzed by means of Southern blot hybridization (iii) in order to be able to distinguish between both possibilities i) By random transposon mutagenesis the cryptic plasmid pAtC58 was provided with a selectable marker. For this purpose the "suicide" plasmid pJB4JI was used as Tn 5 donor for LBA 288, as was described for mutagenesis of *Rhizobium lecuminosarum* (Berlinger et al., Nature (London), 276, 633-634)). By means of conjugation experiments it was proved that in a number of cases Tn 5 was present in LBA 288 on a self-transmissible plasmid. This plasmid appeared to be pAtC58 (transmission frequency $10^{-7}$ per recipient). This newly found quality of pAtC58 to transmit itself was used to determine whether Tn 1882 was present in LBA 1160 or pAtC58. For this purpose LBA 1160 and LBA 1201 (pAtC58::Tn5) were both used as donor strains in cross-fertilization with LBA 285 for mutual comparison. After selection on transconjugants pAtC58::Tn 5, as was expected, appeared to be transferred with a frequency of $10^{-7}$ per recipient. However, no transmission of the $Ap^R$ of Tn 1882 could be shown. This indication formed a strong indication for the assumption that Tn 1882 was not present on the cryptic plasmid pAtC58 in the donor strain LBA 1160.

ii) Plasmids which cannot be maintained stably in one bacterium cell without selective pressure being exerted, belong to the same incompatibility class (inc.). There are therefore plasmids which are incompatible with themselves. If a Tn 5 marked pAtC58 ($Km^R$) is introduced into an *A.tumefaciens* strain with a Tn 1831 marked pAtC58 ($Sp^R$) and the entering plasmid ($Km^R$) is selected for, this causes a loss of the $Sp^R$ marker by incompatibility, which means removal of the plasmid already present, in the greatest part of the transconjugants. Therefore LBA 1160 could be used as recipient in a cross-fertilization with LBA 1201 (pAtC58::Tn 5) as donor. The entering plasmid pAtC58::Tn 5 was selected ($Km^R$) for and in the transconjugants it was checked whether the $Ap^R$, originating from Tn 1882, was lost by incompatibility. It appeared that all $Km^R$ transconjugants preserved their $Ap^R$, which was again a strong indication that Tn 1882 is not positioned on pAtC58 in LBA 1160.

iii) Definite proof for the location of Tn 1882 in LBA 1160 was obtained through Southern blot hybridization experiments, with which raw plasmid preparations of LBA 288, LB 1201 and LBA 1160 were analyzed. The raw plasmid preparations (isolated according to Casse et al., J. Gen. Microbiol. 113, 229-242 (1979)) were separated into their components on agarose gels. The components which were present in the gel as band, were transmitted direct from the gels into nitrocellulose filters (the so-called blot procedure) and thereafter were hybridized with a number of specific radio-active labeled DNA probes. A control Tn 5-probe hybridized with the so-called supercoil DNA band of pAtC58::Tn 5, and with the linear DNA band, in which in addition to disintegrated chromosomal DNA, disintegrated pAtC58::Tn 5 DNA of the blot is present as well. If Tn3, the starting material for Rn 1882 was used as radio-active probe, no hybridization with pAtC58, which is present in LBA 1160, was found.

Figure 3:
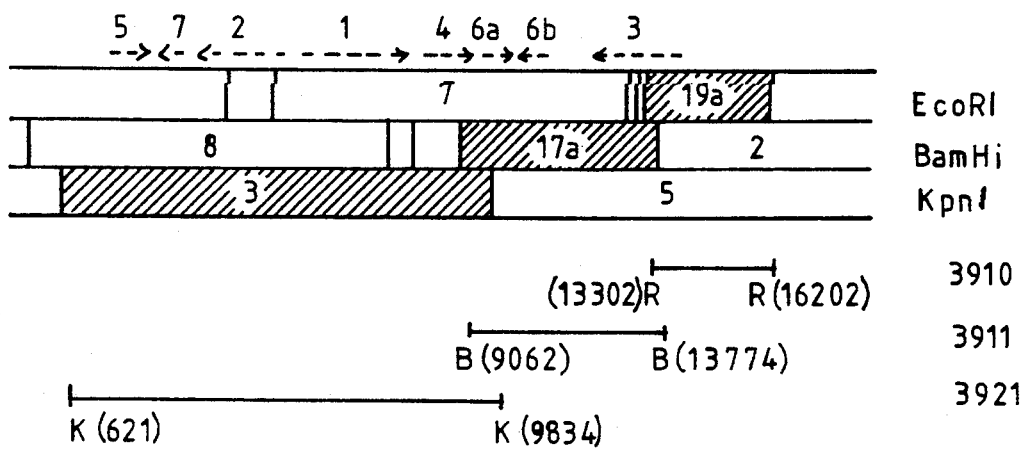

Therefore we concluded from the above that Tn 1882, and therefore the entire T-region of pTi B6, is present in the chromosome of LBA 1160. Southern blot hybridizations, which were carried out with blots on which the total DNA of LBA 1160 was present, fragmented with a number of restriction enzymes and pRAL 3305 and pOTY 8, used as labeled probes, confirmed the correct internal organization of the T-region of the Tn 1882 insertion into LBA 1160 (structure as drawn in FIG. 3).

The stability of the insertion of pRAL 3959 on which Tn 1882 is located, in the chromosome of LBA 1160, was examined by growing the bacteria about 100 generations without selection pressure and by checking whether the resistence markers of pRAL 3959 ($Tc^R$ and $Ap^R$) were maintained. No loss of markers was detected.

LBA 1160 therefore contains the T-region, stably introduced into the chromosome. The virulence functions (Vir-region), which are necessary as well, were introduced through R-prime plasmids (pAL 1818 and pAL 1819) into the strain LBA 1160. Plasmid pAL 1818 contains the vir genes A, B, C, D, and O and pAl 1819 contains the Vir genes A up to and including F and O. After conjugation of LBA 1160 with strains which contain the R-primes and selection of transconjugants LBA 1161 (i.e. LBA 1160 (pAL 1818) and LBA 1162 (i.e. LBA 1160 (pAL 1819)) were created. These strains and the parent strains LBA 1160 and LBA 1818 (pAL 1818) and LBA 1819 (pAL 1819) were tested for their tumour inducing ability on a number of different kinds of plants.

LBA 1160 and LBA 1818 and 1819 only contain one of the components of the binary system and therefore did not give occasion to tumours. However, the LBA 1160 strains with a virulence plasmid (the R-primes mentioned) surprisingly did cause tumours to be created on all tested plants. Behaviour and size of the tumours entirely correspond to those of tumours induced by wild type of Agrobacterium strains. The T-region of the Ti plasmid can therefore be normally introduced from the chromosome of Agrobacterium by means of Vir-region into the genome of higher plant cells.

The observations described are very important for learning to understand the mechanism with which Agrobacterium transfers its T-region to plant cells. The surprising discovery that the T-region is normally transferred, even if it is present in the chromosome of Agrobacterium, means that it is highly improbable that the entire Ti plasmid is introduced into the plant cell during infection and is "processed" there with integration of T-DNA, as was presumed before. Moreover, on the basis of these results, we postulate that recognition and excision of the T-DNA by virulence genes takes place within the bacterium as one of the early stages in the tumour induction process. The so-called border sequences, which border the T-region, could act as recognition signals.

Besides it's fundamental scientific importance this new invention opens new perspectives for the genetic manipulation of higher plant cells. The novelty of this invention and its possibilities for use can best be elucidated by means of FIG. 4. A T-region and Vir-region, which are separately present on 2 separate plasmids, are still able to transfer a T-region or an artificial T-region (and foreign DNA inserted therein) to plant cells, where it is integrated into the genome and is expressed. With the aid of this so-called binary vector system monocotyledonous and dicotyledonous plant cells can be provided with new genetic material (FIG. 4a). Strains containing only the Vir-region or only a T-region on a plasmid (FIG. 4b) or in the chromosome (FIG. 4c) do not cause plant cells to transform. With the present invention it is shown that a T-region, inserted into the chromosome, it still transferred normally to plant cells in a binary system, with a Vir-region present on a separate plasmid (FIG. 4d). By this surprising invention it is also shown that even if a T-region or a Vir-region or both components of Agrobacteria are not located on extrachromosonal replicons (plasmids), but are inserted into the chromosome (situations as drawn in FIGS. 4D, E and F), they can still introduce a T-region or artificial T-region into a plant's genome in an efficient way, so that the claims as set out in European patent application 84 2002396 and Dutch 8401048 can also be applied to these new situations. Such Agrobacteria can be used for the genetic manipulation of the plant cells of dicotyledonous and monocotyledonous plants (Dutch patent application 84 01048).

A process for the incorporation of foreign DNA into the genome of monocotylendonous plants.

The invention relates to a process for the incorporation of foreign DNA into the genome of plants by infecting the plants or by incubating plant protoplasts with Agrobacterium bacteria, containing one or more Ti (tumor-inducing) plasmids.

The bacteria *Agrobacterium tumefaciens* and *Agrobacterium rhizogenes* are naturally capable of genetically engineering plant cells. The bacteria adhere to the plant cell wall and subsequently introduce a fragment of DNA into the plant cell via a process still unexamined. This DNA fragment (the T-DNA) is part, as a T-region in the bacteria, of a large plasmid (120–150 Mdal.), which in case of *A.tumefaciens* is called Ti-plasmid and in case of *A.rhizogenes* is called Ri-plasmid. The T-DNA is integrated into the nucleus genome of the plant cell (Thomashow, M. F. et al. (1980). Proc. Natl. Acad. Sci. USA 77, 6448–6452). Genes located in the T-DNA are expressed there and they induce the plant cell to start behaving like a tumor cell (Ooms, G. et al (1981). Gene 14: 33–50). Meanwhile processes have been developed to couple any type of DNA to the T-region in such a way that it can subsequently be introduced into the plant cell simultaneously with the T-region by means of *A.tumefaciens* (Hille, J. et al. (1983). J.Bacteriol. 154: 693–701 and Hoekema, A. et al. (1983). Nature 303: 179–180). The onc-genes can be removed from the T-region (Hille, J. et al. (1983). Plant Mol. Biol. 2: 155–163 and Zambryski, P. et al. (1983). EMBO J. 2: 2143–2150). This results in vectors which, although being transmitted by the *A.tumefaciens system* to the plant cell, are no longer oncogeneous (Hille, J., et al. (1983). Plant Mol. Biol. 2: 155–163 and Zambryski, P., et al. (1983). EMBO J. 2: 2143–2150). Plant cells transformed by means of these "tamed" vectors are able to regenerate into plantes with new properties (encoded by the genes introduced into the T-region (Zambryski P., et al. (1983), EMBO J. 2: 2143–2150). Literature teaches that the Ti-plasmid can be used as a vector only for dicotyledonous plants, as only dicotyledonous plants respond to *A.tumefaciens* by growing tumours (Lippincott, J. A. & Lippincott, B. B. (1975). Ann. Rev. Microbiol. 29: 377–407). The fact that the cell wall of monocotyledonous plants differs from that of dicotyledonous plants was said to be the cause of this phenomenon (Lippincott, J. A. & Lippincott, B. B. (1980). In: "Bacterial Adherence in Receptors and Recognition" (E. H. Beachley, ed.) pp. 377–396 and Rao, S. S., et al. (1982). Physiol. Plant, 56: 374–380). The prevailing view is therefore that Ti-plasmid would not be suitable as a vector for the genetic engineering of monocotyledonous plants (Flavell, R. & Mathias, R. (1984). Nature 307: 108–109). However, the group of monocotyledonous plants includes some extremely important agricultural and horticultural plants, such as cereals and bulbous plants, e.g. the tulip, daffodil and lily. The analysis described hereinafter was conducted in order to establish whether the prevailing view as to the impossibility of using T-plasmid as a vector for monocotyledonous plants was indeed correct. In this analysis, various kinds of monocotyledonous plants were infected with *A.-tumefaciens* strains, either possessing one of various types of Ti- or Ri-plasmids or containing a combination of such plasmids. Surprisingly, the experiments showed that actually, cells of monocotyledonous plants were indeed transformed by *A.tumefaciens*. These experiments proved for the first time that Ti-plasmid (or plasmids derived therefrom) is suitable for the genetic engineering of monocotyledonous plants.

Experiment

In addition to onc-genes, which induce phytohormone synthesis (Ooma, G., et al. (1981). Gene 14: 33–50 and Garfinkel, D. J., et al. (1981). Cell 27: 143–153), T-DNA also contains genes which encode for enzymes which induce the biosynthesis of "opines". The latter genes are tumour-specific amino acid derivatives, such as octopine and nopaline (Tempé, J. & Goldman, A. (1982). In: "Molecular Biology of Plant Tumors". (G. Kahl & J. Schell, eds.), pp. 427–449).

As opines do not occur in normal plant cells, they can be considered as specific indicators for incorporation and expression of T-DNA in the plant cell, even if there would be no transformation leading to the growth of tumour cells. There are various types of T-DNA that carry genes for enzymes inducing biosynthesis of different opines. Octopine and nopaline T-DNAs, respectively, are the types most commonly known.

A large number of experiments was then conducted, in which monocotyledonous plants from the family of *Liliaceae* (*Chlorophytum capense*) and the family *Amaryllidaceae* (*Narcissus* c.v. Paperwhite) were wounded and subsequently infected with various *A.tumefaciens* strains. The used strains were, LBA288 (avirulent; no Ti-plasmid), LBA1010 (containing an octopine Ti-plasmid), LBA2318 (containing a noplaine Ti-plasmid), LBA1020 (containing an Ri-plasmid), LBA2347 (containing a noplaine Ti-plasmid+Ri-plasmid), LBA1516 (containing an octopine Ti-plasmid with a Vir-mutation; avirulent). After a few weeks plant material was removed from the infected spots and analysed for opines (Otten, L.A.B.M. & Schilperoort, R. A. (1978). Biochem. Biophys. Acta 527: 497=500).

It should be remarked that after infection with virulent strains, often a slight thickening around the wounded area was observed. There was no growth of thick tumours. After infection with avirulent strains, no thickening was observed at all.

Plant material isolated from either non-wounded or wounded but non-infected monocotyledonous plants appears to contain neither octopine nor nopaline. Opines were not found either in plant material isolated from plants infected with the avirulent strains LBA288 or LBA1516. However, plant cells obtained from wound areas infected with virulent *A.tumefaciens* strains almost always appeared to contain opines. After infection with a strain with an octopine Ti-plasmid (LBA1010) octopine appeared to be present, whilst after infection with strains with a nopaline Ti-plasmid (LBA2318, LBA2347) noplaine appeared to be present. The positive results obtained with strain LBA2347 could be reproduced best. All the information combined, rendered the proof that *A.tumefaciens* is capable of transmitting T-DNA to monocotyledonous plant cells and furthermore that T-DNA genes (at any rate those involved—for the enzymos—in the biosynthesis of opines) are expressed in monocotyledonous plant cells. Consequently it can be concluded that Ti-plasmid is suitable as a vector for monocotyledonous plant cells. Furthermore it can be concluded that the regulator zones which induce the expression of opine synthesis genes are functional and therefore suitable as building stones for making chimaeric genes which should be made to express in monocotyledonous plant cells.

plant cells, and in particular the genes for octopine synthesis and noplaine synthesis can be used.

| | | Plasmids and bacterium strains used. | |
|---|---|---|---|
| | | SPECIFICATIONS | SOURCE |
| PLASMIDS | RESISTENCE MARKERS | | |
| pOTY 8 | Ap | | Hirsch |
| pRAL 3101 | CmKm | pACYC 184 derivative containing unique KpnI-site | this publication |
| pRAL 3102 | Cm | pACYC 184 sender BamHI site | this publication |
| pRAL 3103 | ApTc | pTR 262::Tn 3 ($\Delta$ 5–65) | this publication |
| pRAL 3305 | Tc | pACYC 184 with 1600 bp chromosomal EcoRI DNA fragment. | this publication |
| pRAL 3910 | ApEm | pBR325, cloned pTiB6 EcoRI fragment 19a | this publication |
| pRAL 3911 | Ap | pBR313 in which cloned pTiB6 BamHI fragment 17a | this publication |
| pRAL 3921 | Cm | pRAL 3101, in which cloned pTiB6 KpnI fragment 9 | this publication |
| pRAL 3945 | ApTc | pTR262::Tn1880 | this publication |
| pRAL 3955 | ApCm | pRAL 3102::Tn1880 | this publication |
| pRAL 3956 | ApCm | pRAL3955 in which cloned pTiB6 BamHI fragment 17a | this publication |
| pRAL 3957 | ApCm | pRAL3956 in which cloned pTiB6 KpnI fragment 9 | this publication |
| pRAL 3958 | ApKm | pRK2013::Tn 1882 | this publication |
| pRAL 3959 | ApTc | pRAL 3305::Tn 1882 | this publication |
| pAL 1155 | ApKm | R772::Tn 1880 | this publication |
| pAL 1157 | ApKm | p772::Tn 1882 | this publication |
| R772 | Km | | Hedges |
| pRK 2013 | Km | | Figurski |
| E. coli strains | relevant markers | | |
| KMBL 1164 | Pro$^-$Thi$^-$ | | vd Putte |
| HP 3435 | Bio$^-$Rif$^R$ | | Pannekoek |
| A. tumefaciens strains | | | |
| LBA 285 | Spc$^R$ | | |
| LBA 288 | Rif$^R$ | | |
| LBA 1010 | Rif$^R$ | pTiB6 | |
| LBA 1160 | Rif$^R$ ApTc. | LBA 288; Tn 1882 in the chromosome described here | |
| LBA 1161 | Rif$^R$ApTc | LBA 1160 (pAL 1818) | |
| LBA 1162 | Rif$^R$ApTc | LBA 1160 (pAL 1819) | |
| LBA 1201 | Km | pAtC58:: Tn5. | " |
| LBA 1223 | KmSpc$^R$ | LBA 285 (pAtC58:: Tn5). | " |
| LBA 1224 | Rif$^R$ApKmTc | LBA 1160 (pAtC58::Tn5). | " |
| LBA 1818 | | pAL 1818 | |
| LBA 1819 | | pAL 1819 | |
| LBA 4404 | Rif$^R$ | pAL 4404 | |
| LBA 4434 | Rif$^R$ApKm | LBA 4404 (pAL 1050) | |
| LBA 4440 | Rif$^R$ApKm | LBA 4404 (pAL 1157) | " |

Consequently, the invention relates to a process as mentioned in the introduction, which process is characterized in that monocotyledonous plants are infected or monocotyledonous plant protoplasts are incubated with Agrobacterium bacteria, in which the Ti-(tumor-inducing)plasmid is a stable cointegrate plasmid from a plasmid R772 and from a plasmid pTiB6 with incorporated foreign DNA in the T-region of the Ti-component of the cointegrated plasmid.

Preferably Agrobacterium bacteria are used, containing at least one plasmid which has the Vir-region of a Ti(tumor-inducing)plasmid but no T-region, and at least one other plasmid which has a T-region with incorporated foreign DNA but no Vir-region.

For those Agrobacterium bacteria that are suitable for the process according to the invention and also for the way in which these bacteria can be obtained, rights have already been claimed in the non-prepublished European patent application 84200239.6.

The regulator regions of T-DNA genes can be used to make foreign genes express in monocotyledonous

We claim:

1. Agrobacteria comprising a T-region and a Vir-region in their DNA, the T-region being stably integrated into the bacterial chromosome.

2. Agrobacteria comprising a T-region and a Vir-region in their DNA, the Vir-region being stably integrated into the bacterial chromosome.

3. A process for the transfer of recombinant DNA into the cells or protoplasts of plants selected from the group consisting of dicotyledonous plants and monocotyledonous plants of the families Liliaceae and Amaryllidaceae, said process comprising infecting the plants or plant cells, or incubating protoplasts from the plants, with Agrobacterium bacteria which contain in their genetic material a Vir-region from the Ti plasmid of Agrobacterium and at least one T-region, wherein said T-region comprises said recombinant DNA flanked on both sides by border sequences as present in wild-type of Agrobacterium, and wherein said Vir-region is integrated into the chromosome of said Agrobacterium bacteria prior to said infecting or incubating step.

4. The process, as in claim 3, wherein the plants are dicotyledonous plants.

5. A process for the transfer of recombinant DNA into the cells or protoplasts of plants selected from the group consisting of dicotyledonous plants and monocotyledonous plants of the families Liliaceae and Amaryllidaceae, said process comprising infecting the plants or plant cells, or incubating protoplasts from the plants, with Agrobacterium bacteria which contain in their genetic material a Vir-region from the Ti plasmid of Agrobacterium and at least one T-region, wherein said T-region comprises said recombinant DNA flanked on both sides by border sequences as present in wild-type T-region of Agrobacterium, and wherein each of said T-region is integrated into the chromosome of said Agrobacterium bacteria prior to said infecting or incubating step.

6. A process as claimed in claim 5, wherein the plants infected or the plant protoplasts incubated with the Agrobacterium bacteria are dicotyledonous plants or plant protoplasts from dicotyledonous plants.

* * * * *

UNITED STATES PATENT AND TRADEMARK OFFICE
CERTIFICATE OF CORRECTION

PATENT NO. : 5,149,645
DATED : September 22, 1992
INVENTOR(S) : Andre Hoekema, et al It is certified that error appears in the above-indentified patent and that said Letters Patent is hereby corrected as shown below:

On the title page:

item [75] Inventors: after "Hoekema," change "Brisane" to --Brisbane, California-- after "Hooykaas, Leiden," insert --Netherlands-- after "10c 2334 CD, Leiden," delete "all of"

item [73] Assignees: change "Scilperoort" to --Schilperoort-- item [30] Foreign Application Priority Data change "8491780" to --8401780--

Signed and Sealed this

Fifteenth Day of March, 1994

Attest:

BRUCE LEHMAN

Attesting Officer    Commissioner of Patents and Trademarks